United States Patent [19]
Speckmann

[11] Patent Number: 5,209,660
[45] Date of Patent: May 11, 1993

[54] DENTAL APPLIANCE WITH IMPROVED CONNECTING ELEMENT

[75] Inventor: Jürgen Speckmann, Hagen, Fed. Rep. of Germany

[73] Assignee: Si-tec GmbH Dental-Spezial-Artikel, Gevelsberg, Fed. Rep. of Germany

[21] Appl. No.: 847,897

[22] Filed: Mar. 6, 1992

[30] Foreign Application Priority Data

Mar. 8, 1991 [DE] Fed. Rep. of Germany ... 9102797[U]

[51] Int. Cl.⁵ ..................... A61C 13/12; A61C 13/225
[52] U.S. Cl. ...................... 433/181; 433/182
[58] Field of Search ............... 433/172, 177, 181, 182, 433/183, 191

[56] References Cited

U.S. PATENT DOCUMENTS

| 2,271,796 | 2/1942 | Eckman | 433/182 |
| 3,117,377 | 1/1964 | Poveromo | 433/182 |
| 3,710,446 | 1/1973 | Poveromo | 433/182 |
| 3,787,975 | 1/1974 | Zuest | 433/182 |
| 4,196,516 | 4/1980 | Poveromo | 433/182 |
| 4,767,329 | 8/1988 | Schiwiora et al. | 433/181 |

Primary Examiner—Gene Mancene
Assistant Examiner—Nicholas D. Lucchesi
Attorney, Agent, or Firm—Herbert Dubno

[57] ABSTRACT

A dental appliance or prosthesis has its removable member connected to its fixed member by a clamping rib which is engaged in a groove and can have longitudinal wall portions separated from a base by respective slits, bulged outwardly by a cap screw whose shank is threadedly engageable in the base of the rib and whose head bears against conical recesses along inner surfaces of the longitudinal wall portions of the rib.

8 Claims, 6 Drawing Sheets

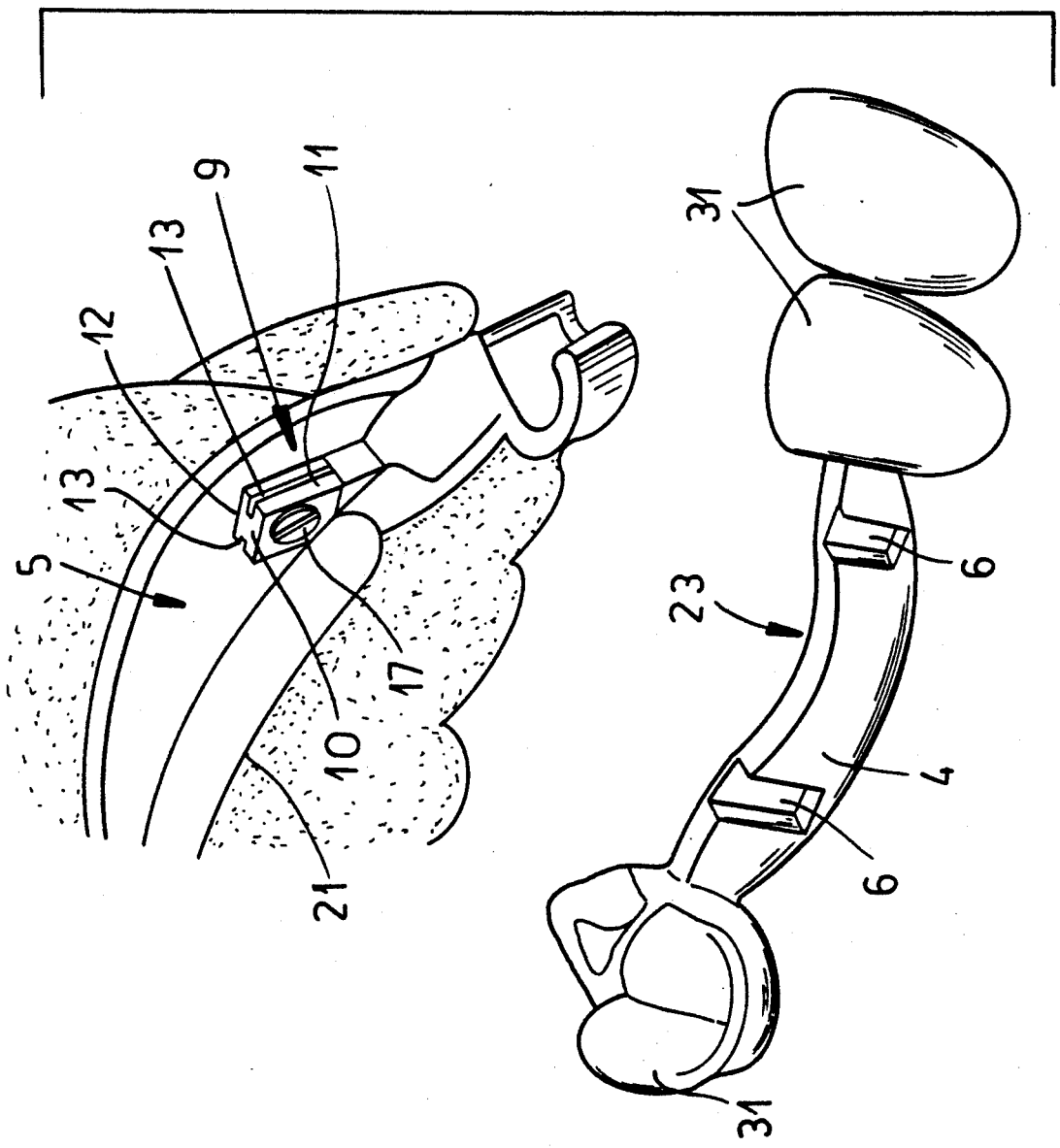

DENTAL APPLIANCE WITH IMPROVED CONNECTING ELEMENT

FIELD OF THE INVENTION

My present invention relates to a dental appliance or prosthesis and, in general, to any structure which is to be mounted, usually detachably, on the jaw of a patient and, more particularly, upon a tooth, tooth stump or implant. Specifically, the invention relates to the connection of the removable member of the appliance or prosthesis to the fixed member thereof and to a thrust-distribution arm for dental prostheses, a connecting element for dental prostheses or the like utilizing the improved connecting assembly.

BACKGROUND OF THE INVENTION

In the use of a so-called thrust distribution ar for dental prostheses, it is common practice to provide a tooth stump with a crown which has a generally semi-cylindrical or semicircular cross section support surface receivable in a complementary recess of the thrust distribution arm and an axially opening and laterally opening groove adjacent the supporting surface of the crown in which a complementary rib on the thrust distribution arm is axially shiftable. A clamping rib is axially shiftable in another groove on the other side of the surface.

The thrust distribution arm to be part of a dental prosthesis, for example, in a bridge between two tooth stumps.

For fixing the thrust distribution arm with its recess to the corresponding support surface of the crown on one of these tooth stumps, the prosthesis is placed over the crown and the ribs are slid into the respective grooves. An adhesive composition may be inserted or some other means used to lock the prosthesis in place. The drawback of such means is that it generally has projecting parts which transfer with subsequent removal of the prosthesis, can serve as locations for accumulation of food residues or the like so that scale or plaque formation can occur with consequent irritation of the gums. The earlier configurations of the rib and groove constructions also were not capable of preventing canting of the prosthesis so that often the prosthesis was not precisely positioned and could not be effectively used without damage to the prosthesis or damage to the support stumps or inconvenience of the user.

Similar drawbacks applied to connecting elements utilized for other dental prostheses. For example, it is desirable to provide between two tooth stumps of which are material or synthetic, e.g. formed by implants, a bar bridging the crowns and onto which a prosthesis in the form of a supercrown is mounted. The supercrown may form part of a much larger prosthesis. It is desirable to provide rib and groove connections between the crown along the respective bar. In this case as well, the prosthesis could have a rib fitting into an open groove of such a bar, the prosthesis having a channel which receives the bar so that the bar also serves to hold the prosthesis in proper orientation.

OBJECTS OF THE INVENTION

It is, therefore, the principal object of the present invention to provide an improved connecting assembly between a member fixed in the jaw of a user or patient, namely, a crown on a tooth stump or an implant, and another member which can form part of a dental prosthesis, for example, a super or upper crown, a thrust distributing element, a bridge or the like, whereby drawbacks of earlier systems are avoided.

Another object of the invention is to provide a dental appliance or prosthesis with improved means for anchoring the removal part so that the accumulation of food residues and scaling can be avoided and plaque buildup minimized.

Still another object of the invention is to provide improved connection of the fixed and removable parts of a dental prosthesis whereby tilting of the prosthesis in use is avoided and the prosthesis can be more accurately positioned on a long term basis.

With a further object of the invention is to provide a dental appliance or prosthesis in which a thrust distribution arm is mounted on a crown or a removable prosthesis is engaged over a bar connecting material or artificial support elements anchored in the jaw which permits a stepless adjustability of the clamping force with which the removable member engages the fixed member, without the need for adhesive compositions or other projecting and potentially irritating materials o articles and which will allow the prosthesis to be fitted to the fixed member free from any tilting or canting potential.

SUMMARY OF THE INVENTION

These objects are attained, in accordance with the invention by providing the connecting element so that it is in the form of a generally rectangular clamping rib having four wall portions extending from a base and so that the base lies substantially in a plane of the support surface of the thrust distribution arm, the two longitudinal side walls of the clamping rib proximal to the base are separated from the latter and are only connected to the base in the regions of their junctions with the smaller side walls, the base is centrally provided with a threaded bore in which the threaded shank of a cap screw is screwed, the head of the cap screw engages inner surfaces of the opposite longitudinal side wall portions, and these inner surfaces at least where they are engaged by the head, conically converge toward the base.

The tooth stump or the bar connecting two artificial or material tooth stumps can thus be formed with a groove open axially and laterally and into which the clamping rib can be form fittingly engaged axially and the rib may have its longitudinal wall portions flexed outwardly by the screw so that the degree of such flexure controls the frictional engagement between the rib and the flanks of the groove. The rib thus forms a steplessly actuatable friction element which, because of its small size, can be used in practically all dental prostheses or dental appliance construction, including telescope crowns, conical crowns, for tooth stumps provided with the groove directly and without a crown, for bars of all shapes interconnecting tooth stumps, their respective crowns or implants or between implants and material tooth stumps or crowns, etc.

It can be used for example, for large scale reconstruction of teeth in the form of bridges spanning many teeth or a prosthesis which has a considerable span between support posts and, substantially, for all parodontal needs. Since the friction can be adjusted to suit all needs, the connecting element can be used for all types of implants and for various combinations of prostheses with support implants or tooth stumps.

The adjustment of the friction force is effected in a stepless manner since the cap screw can be tightened to a greater or lesser extent in its threaded bore, the longer side wall members of the clamping rib being bulged outwardly to a greater or lesser extent to vary the clamping force between the side walls and the corresponding flanks of the receiving groove.

It is important that the outwardly bulging take place primarily proximal to the base rather than at free ends which could cause canting of the prosthesis or damage to the assembly. The thrust distribution arm can take up substantially all of the lever forces applied to the prosthesis. When the prosthesis is removed, the cervical edges are free so that they are easily cleaned. Irritating elements are not found in the region of the crown and essentially the thrust distribution arm can be intercoronal.

More specifically, a dental prosthesis according to the invention can comprise:
a first member fixed in a jaw of a patient;
a second member axially insertable over the first member and adapted to be removable mounted thereon; and
coupling means for anchoring the second member on the first member, the coupling means including:
  an axially and laterally open groove formed in one of the members and having a pair of axially extending flanks,
  a shaped surface adjoining the groove and formed on the one of the members,
  a complementary surface on the other of the members formfittingly engaging the shaped surface upon assembly of the second member on the first member,
  a substantially rectangular clamping rib of the other of the members adjacent the complementary surface, substantially complementary to and receivable in the groove, and having
    a base lying substantially in a plane of the complementary surface,
    four wall portions extending away from the base and including two longitudinal wall portions juxtaposed with the flanks,
    means separating the longitudinal wall portions from the base proximal to the base whereby the longitudinal wall portions can flex outwardly,
    a threaded bore formed centrally of the base between the longitudinal wall portions, and
    a threaded screw threaded into the bore and having a head bearing against the longitudinal wall portions to flex the longitudinal wall portions outwardly,
    the longitudinal wall portions having substantially conical inner surfaces engaged by the head.

Preferably the one of the members is the first member and the other of the members is the second member, the first member being a crown, implant or tooth stump directly, while the second member is a thrust arm connected to a prosthesis structure, the prosthesis structure itself or some other member attached to the prosthesis. Where the first member is a bar bridging teeth, stumps or implants, the second member has a groove formed with the complementary surface and receiving the bar. In most instances the second member will be formed with a socket receiving the first member and designed by the complementary surfaces.

The shaped and complementary surfaces can be of circular segmental cross section and can be substantially cylindrical or conical surface segments. Advantageously the inner surfaces are formed by recesses corresponding in curvature to a circular shape of the screw head and conically diverging in a direction in which the screw is tightened.

BRIEF DESCRIPTION OF THE DRAWING

The above and other objects, features and advantages of my invention will become more readily apparent from the following description, reference being made to the accompanying highly diagrammatic drawing in which:

FIG. 8 is a diagrammatic perspective view illustrating a bridge appliance (inverted) and the shaft member to which that appliance is to be anchored.

SPECIFIC DESCRIPTION

Figure 1:
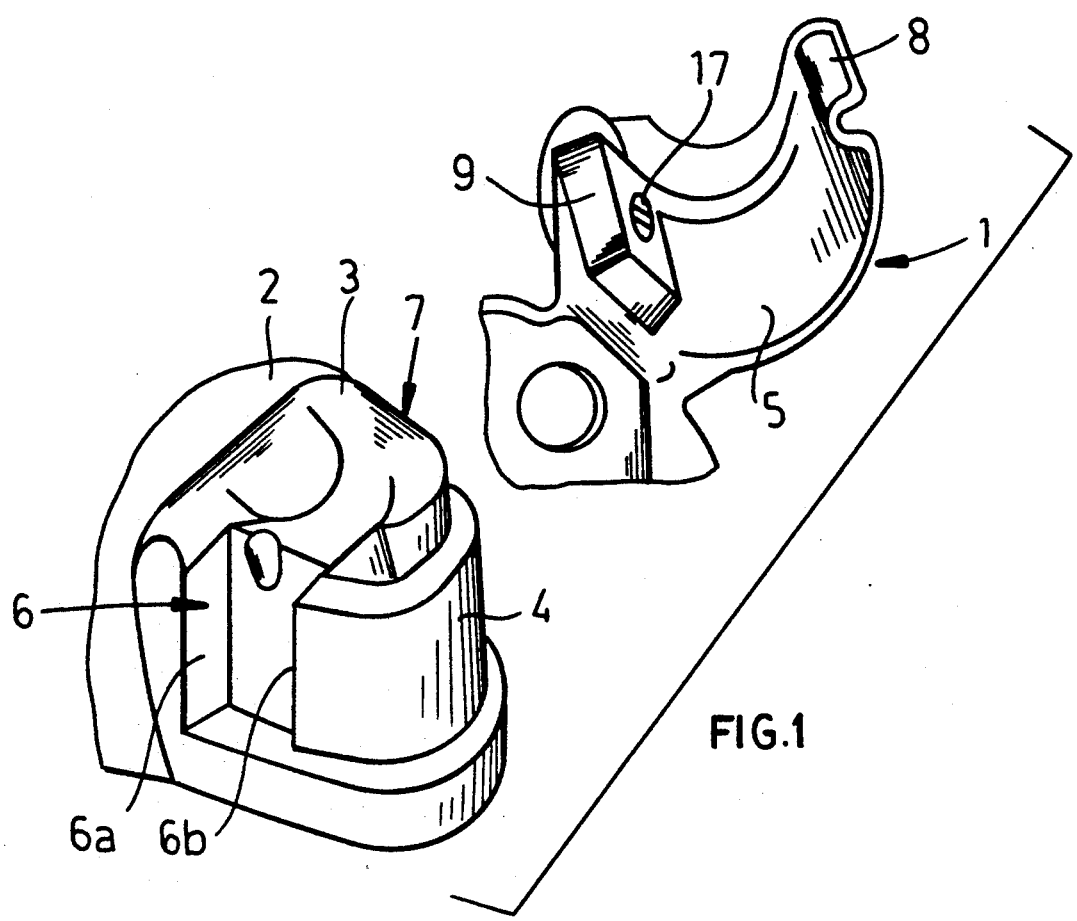
FIG. 1 is an exploded perspective view of a crown and the thrust distribution arm adapted to fit thereover in accordance with one embodiment of the invention.

Referring first to FIGS. 1 to 5, it can be seen that a thrust distribution arm 1 of a dental prosthesis, for example, a bridge, can be fitted onto a crown 3 which has previously been applied to a tooth stump 2 and forming the fixed member of the coupling. The exposed surface 3 of the crown facing the prosthesis has a support surface 4 which is shaped, e.g. with a semicircular cross section and a cylindrical or conical configuration. This surface 4 is engaged by a complementary surface 5 of the thrust distribution arm 1 forming a cavity or socket in which the crown 3 is received. At opposite circumferential ends of the surface 4, axially and outwardly opening grooves 6 and 7 are provided in which complementary ribs 8 and 9 are axially slidable. The rib 8 is slidable axially into the groove 7 and the rib 9, which constitutes the clamping rib, is slidable axially into the axial groove. The latter has flanks 6a and 6b which will be mentioned again below.

The clamp rib 9 is shown in detail in FIGS. 2 to 5 and is integrated in the thrust distribution arm 1 which is seen in FIG. 1.

The clamping rib 9 is formed substantially as a rectangular parallelepiped and has 4 wall portions 10, 11 extending from a base 12 which lies in the plane of the surface 5 of the thrust distribution arm 1.

Figure 2:
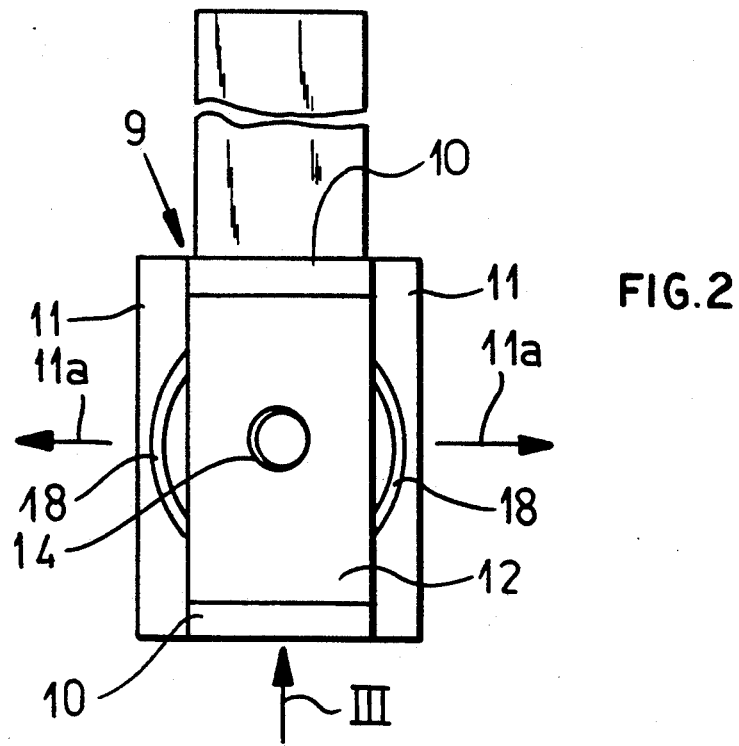
FIG. 2 is an elevational view of the clamping rib of a thrust distribution arm.
Figure 4:
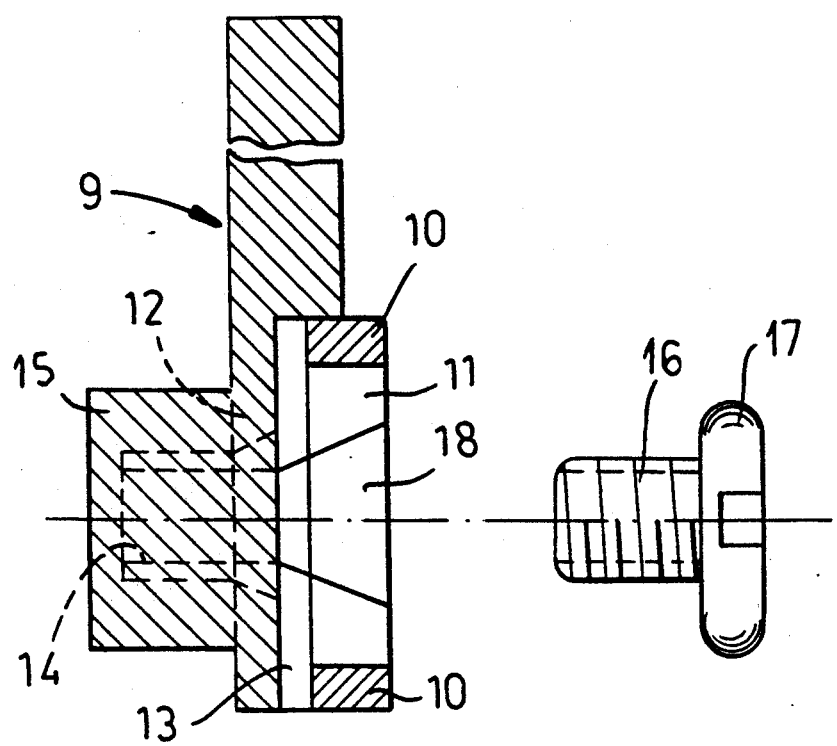
FIG. 4 is a view of the thrust distribution arm and its clamping rib in an exploded cross section.
Figure 3:
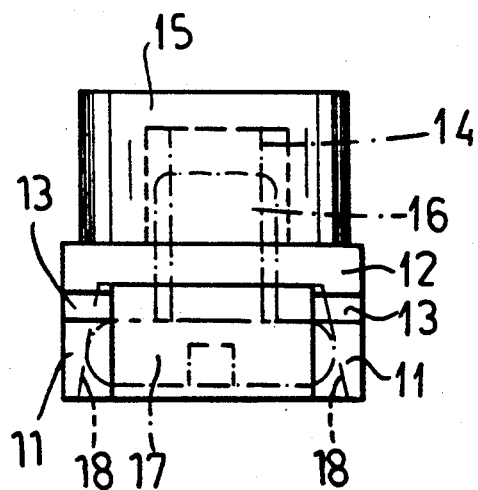
FIG. 3 is a view taken in the direction of the arrow III of FIG. 2.
Figure 5:
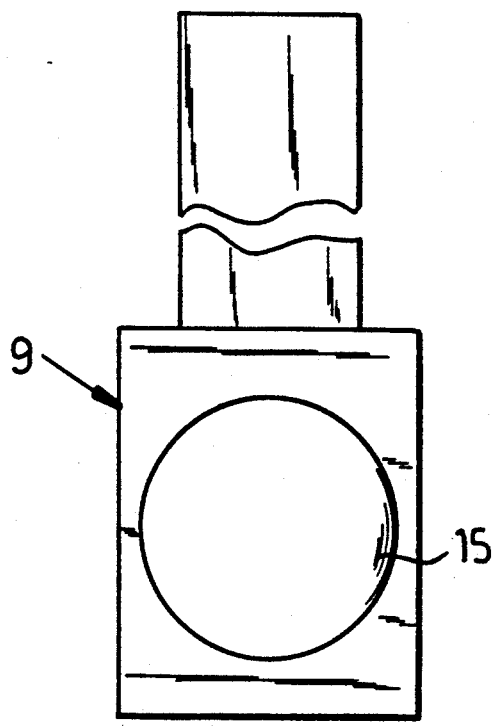
FIG. 5 is a rear elevational view of the thrust distribution arm.

The 2 longitudinal side wall portions 11 of the rib 9 are separated proximal to the base 12 from the latter by separating slits 13 so that these walls can bulge outwardly as represented by the arrows 11a in FIG. 2. They are connected with the base 12 only at their junctions with the small side walls 10.

Centrally of the base 12 there is provided a threaded bore 14 which can extend into a body 15 of the arm or prosthesis behind the base 12. A threaded shank 16 of a cap screw can be threaded into the bore 14 and has a head 17 which lies against inner surfaces of the opposite side walls 11. These inner surfaces, represented at 18, are segments of a cone as is apparent from FIG. 3. As can be seen from FIG. 2, the inner surface 18 conforms to the curvature of a circular head 17 of the screw.

As the screw 17, 16 is tightened in the bore 14, the walls 11 are bulged outwardly. In this manner the friction force between the clamping rib 9 and the flank 6a and 6b of the groove 6 can be steplessly adjusted and a secure seat provided for the rib in the groove and hence for the prosthesis on the fixed member of the dental appliance.

Upon removal of the prosthesis in the axial direction, the cervical edge remains free and can be easily cleaned by irrigation or the like. A significant advantage of the device of the invention is that by the screwing of the screw 17, 16 and the outward bulging of the side walls 11, there is no significant spreading at the free ends of the side walls so that no sharp edges are there formed which can be detrimental upon insertion of the clamping rib in the respective groove.

Figure 6:
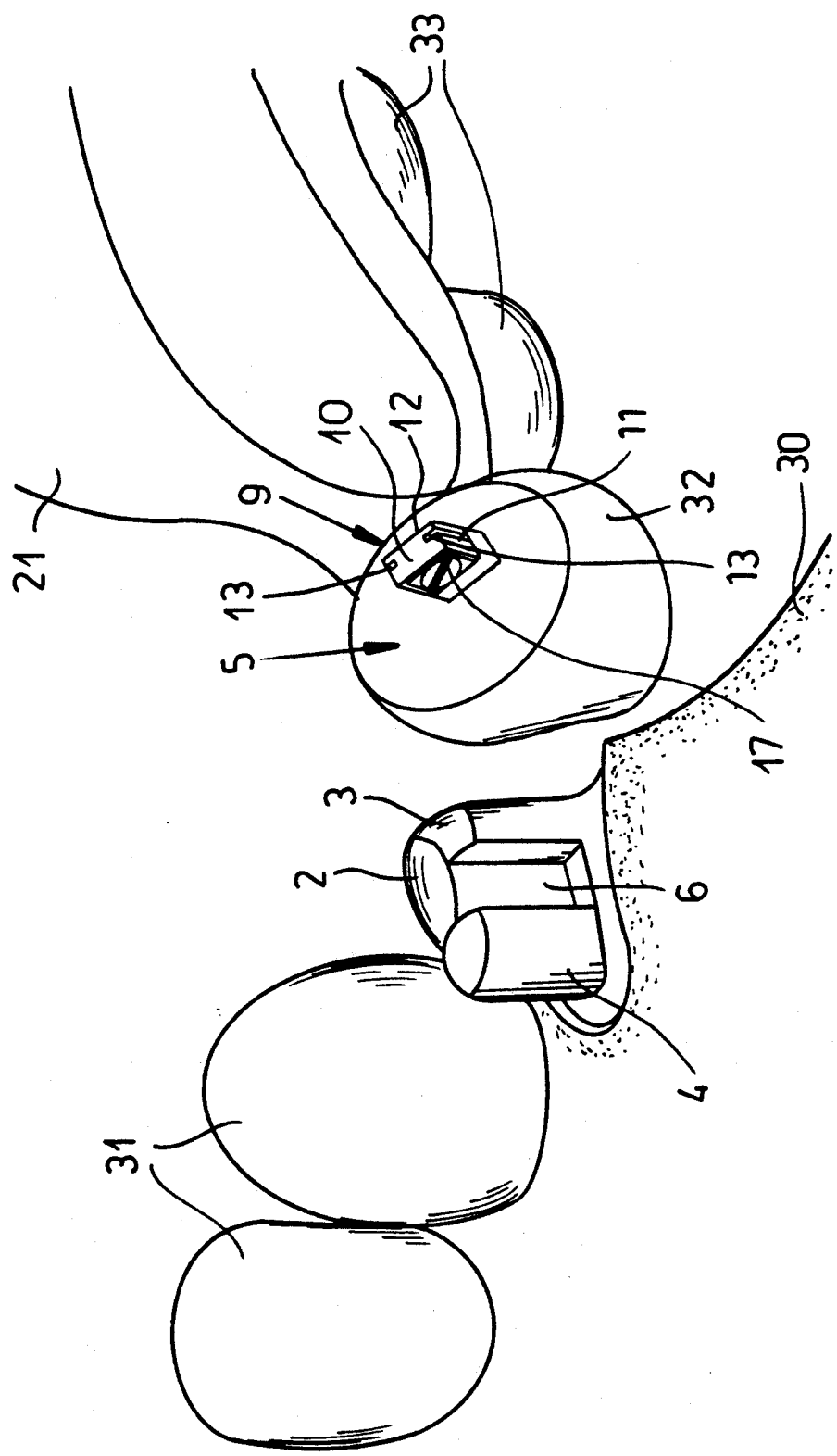
FIG. 6 is a perspective view of a crown in the lower jaw of the patient showing, also in a perspective view, but inverted with respect to the crown a prosthesis whose connecting element is to engage in the groove in the crown.

In FIGS. 6 through 8, we show other embodiments of the invention.

In FIG. 6, for example, the lower jaw has been represented at 30 and can be seen to have material teeth 31 and a tooth stump 2 to which a crown 3 has been applied. The crown 3 forms a support for an overcrown 32 forming part of a prosthesis 21 which can carry further synthetic teeth 33.

Figure 7A:
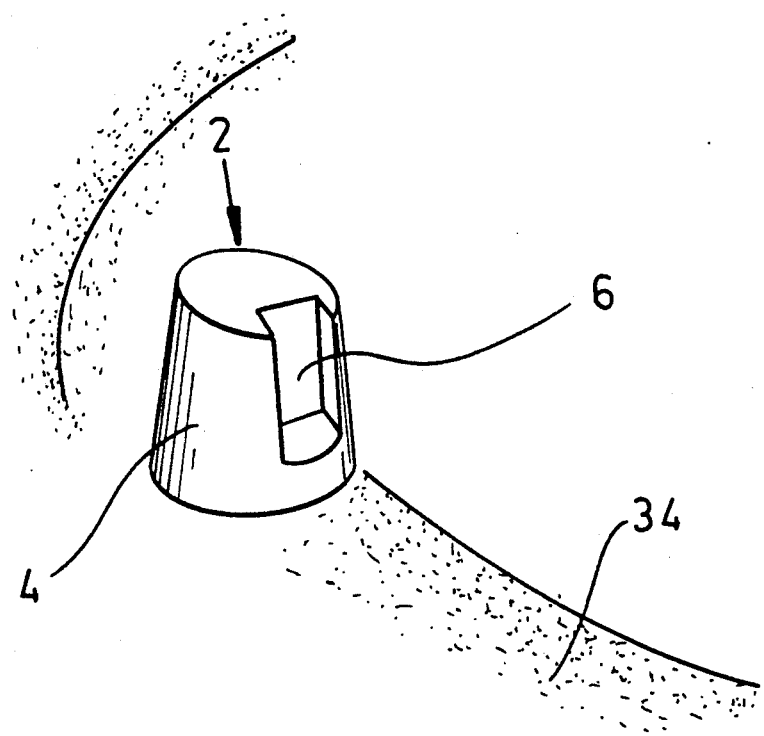
FIG. 7a is a perspective view showing a tooth stump to be engaged by a prosthesis.
Figure 7B:
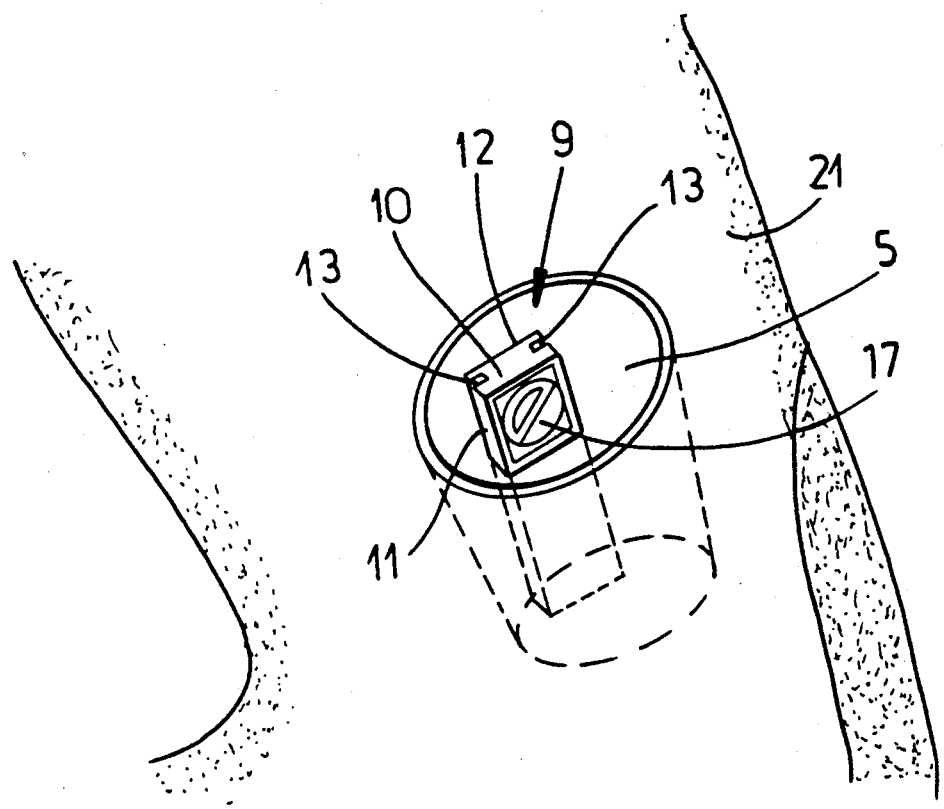
FIG. 7b is a diagrammatic perspective view inverted with respect to FIG. 7a, showing a prosthesis adapted to feed over the tooth stump of FIG. 7a and having a connecting element engaging same.

The crown 3 has a support surface 4 which, as previously described, can be received in the complementary surface formed by a socket 5 by a kind of telescopic crown when the member 32 is fed over the members 2 and 3. The crown 3, as in the embodiment of FIGS. 1 to 5, comprises an axially open and laterally open groove 6. Into this groove 6, a clamping rib 9 can be slid when the prosthesis 21 is set onto the crown 3. The clamping rib 9, as has been described in connection with the embodiment of FIGS. 1 to 5, has wall portions 10 faced to the base 12 and wall portions 11 which are separated by slits 13 from the base so that the wall portions 11 can be spread apart by the screw whose head is seen at 17 in FIG. 6. This spreading action is effected in the same manner as has been described in connection with FIGS. 1 to 5. In the embodiment of FIGS. 7a and 7b, the lower jaw 34 is seen to be provided with an implant which can form a synthetic tooth stump 2 which has the support surface 4 and the groove 6 previously described. Alternatively, the groove 6 can be formed in a material tooth stump as desired. In either case, the synthetic or material tooth stump 21 is receivable in a socket 5 defining the complementary surface for the surface 4 in a prosthesis 21 shown in FIG. 7b.

The clamping rib 9 is formed on the complementary wall 5 so that it base is coplanar with the surface 5. The clamping rib 9 has its side walls 11 expanded by the screw whose head is shown at 17 in FIG. 7b in the same manner as has been described in connection in FIGS. 1 and 6. In the embodiment of FIG. 8, a bar 23 is provided between the material teeth 31 or crowns formed on the material 31 or on implants which are entirely equivalent to the material teeth 31 as supports for the bar 23.

The bar 23 has the shaped surface 4 and is received in a groove or channel forming the complementary surface 5 of the prosthesis 21. The bar 23 has a plurality of axial grooves 6 in which respective clamping ribs 9 of the prosthesis can engage upon the fitting of the prosthesis 21 upon the bar 23. Of the clamping ribs 9 required for engagement with the grooves 6, only one has been illustrated in FIG. 8. The construction of these ribs and there frictional engagement with the grooves corresponds to those which have been described in connection with the previous figures. In all embodiments, the wall portions 10 and 11 can be formed unitarily with the base 12, i.e. in one piece therewith.

I claim:

1. A dental prosthesis, comprising:
   a first member fixed in a jaw of a patient;
   a second member axially insertable over said first member and adapted to be removably mounted thereon; and
   coupling means for anchoring said second member on said first member, said coupling means including:
   an axially and laterally open groove formed in said first member and having a pair of axially extending flanks,
   a shaped surface in the form of a substantially cylindrical surface segment adjoining said groove and formed on said first member,
   a complementary surface in the form of another substantially cylindrical surface segment on said second member formfittingly engaging said shaped surface upon assembly of said second member on said first member,
   a substantially rectangular clamping rib on said second member adjacent said complementary surface, substantially complementary to and receivable in said groove, and having
   a base lying substantially in a plane of said complementary surface,
   four wall portions extending away from said base and including two longitudinal wall portions juxtaposed with said flanks,
   means separating said longitudinal wall portions from said base proximal to said base whereby said longitudinal wall portions can flex outwardly,
   a threaded bore formed centrally of said base between said longitudinal wall portions, and
   a threaded screw threaded into said bore and having a head bearing against said longitudinal wall portions to flex said longitudinal wall portions outwardly,
   said longitudinal wall portions defining a substantially conical inner surface engaged by said head.

2. The dental prosthesis defined in claim 1 wherein said first member is a crown.

3. The dental prosthesis defined in claim 1 wherein said first member is an implant.

4. The dental prosthesis defined in claim 1 wherein said second member is a thrust arm connected to a prosthesis structure to be mounted on said first member.

5. The dental prosthesis defined in claim 1 wherein said first member is a bar bridging teeth and said second member has a groove formed with said complementary surface and receiving said bar.

6. The dental prosthesis defined in claim 5 wherein said second member has a plurality of said clamping ribs and said bar is formed with a plurality of grooves each receiving a respective one of said clamping ribs.

7. The dental prosthesis defined in claim 1 wherein said second member is formed with a socket receiving said first member and defined by said complementary surface.

8. The dental prosthesis defined in claim 1 wherein said inner surface is formed by recesses corresponding in curvature to a circular shape of said head and conically converging in a direction in which said screw is tightened.

* * * * *